(12) United States Patent
Schultz

(10) Patent No.: US 7,311,695 B1
(45) Date of Patent: Dec. 25, 2007

(54) SPLASH SHIELD SYSTEM

(76) Inventor: Joseph P. Schultz, 5385 Peachtree Dunwoody Rd., NE., Atlanta, GA (US) 30342

( * ) Notice: Subject to any disclaimer, the term of this patent is extended or adjusted under 35 U.S.C. 154(b) by 1 day.

(21) Appl. No.: 11/317,758

(22) Filed: Dec. 23, 2005

Related U.S. Application Data

(63) Continuation-in-part of application No. 10/245,241, filed on Sep. 17, 2002, which is a continuation-in-part of application No. 10/123,966, filed on Apr. 16, 2002, and a continuation-in-part of application No. 09/484,666, filed on Jan. 18, 2000, now abandoned.

(51) Int. Cl.
*A61M 35/00* (2006.01)
*A61M 31/00* (2006.01)

(52) U.S. Cl. ............... 604/289; 604/296; 604/310; 604/311; 604/268

(58) Field of Classification Search ............ 604/289, 604/300, 290, 296, 311–313, 263, 192, 35, 604/36, 315–316, 23; 433/80, 96, 116
See application file for complete search history.

(56) References Cited

U.S. PATENT DOCUMENTS

| | | | |
|---|---|---|---|
| 3,648,696 | A | 3/1972 | Keith |
| D295,380 | S | 4/1988 | Virag et al. |
| 4,769,003 | A | 9/1988 | Stamler |
| 4,898,588 | A | 2/1990 | Roberts |
| 5,030,214 | A | 7/1991 | Spector |
| 5,078,694 | A | 1/1992 | Wallace |
| D344,133 | S | 2/1994 | Stamler |
| D345,016 | S | 3/1994 | Stamler |
| 5,735,833 | A | 4/1998 | Olson |
| 5,795,324 | A | 8/1998 | Morse |
| 5,830,197 | A * | 11/1998 | Rucinski ............ 604/290 |
| 5,941,859 | A | 8/1999 | Lerman |
| 6,093,182 | A | 7/2000 | Lampropoulis et al. |
| 6,210,381 | B1 | 4/2001 | Morse |
| 6,293,929 | B1 | 9/2001 | Smith et al. |
| 6,402,724 | B1 | 6/2002 | Smith et al. |

OTHER PUBLICATIONS

Judd Hollander, Wound Registry: Development and Validation, article, May 1995, Annals of Emergency Medicine.
Richard Edlich, Wound Irrigation, editorial, Jul. 1994, Annals of Emergency Medicine.
John Howell, Outpatient Wound Preparetion and Care: a National Survey, Aug. 1992, Annals of Emergency Medicine, article.
Adam Singer, Pressure Dynamics of Various Irrigation Techniques Commonly Used in theEmergency Department, Jul. 1994, Annals of Emergency Medicine, article.
Judd Hollander, Irrigation of Facial and Scalp Lacerations: Does it Alter Outcome?, Jan. 1998, Annals of Emergency Medicine, article.
Thomas Stephenson, Cleansing the Traumatic Wound by High Pressure Syringe Irrigation, article, Jan. 1976, JACEP, vol. 5, No. 1.
Carey Chisholm, Comparison of a New Pressurized Saline Cannister Versus Syringe Irrigation for Laceration Cleansing in the Emergency Department, article, Nov. 1992, Annals of Emergency Medicine.
Richard Edlich, Principles of Emergency Room Management, article, Dec. 1988, Annals of Emergency Medicine.
Jeffrey Morse, Wound Infection Rate and Irrigation Pressure of Two Potential New Wound Irrigation Devices: The Port and the Cap, article, Jan. 1988, American Journal of Emergency Medicine, vol. 16, No. 1.

* cited by examiner

*Primary Examiner*—Jacqueline F. Stephens
(74) *Attorney, Agent, or Firm*—Stoneman Volk Patent Group; Martin L. Stoneman; Michael D. Volk, Jr.

(57) ABSTRACT

A splash shield system for use in combination with various irrigation sources, particularly wide mouth irrigation squeeze bottles.

14 Claims, 11 Drawing Sheets

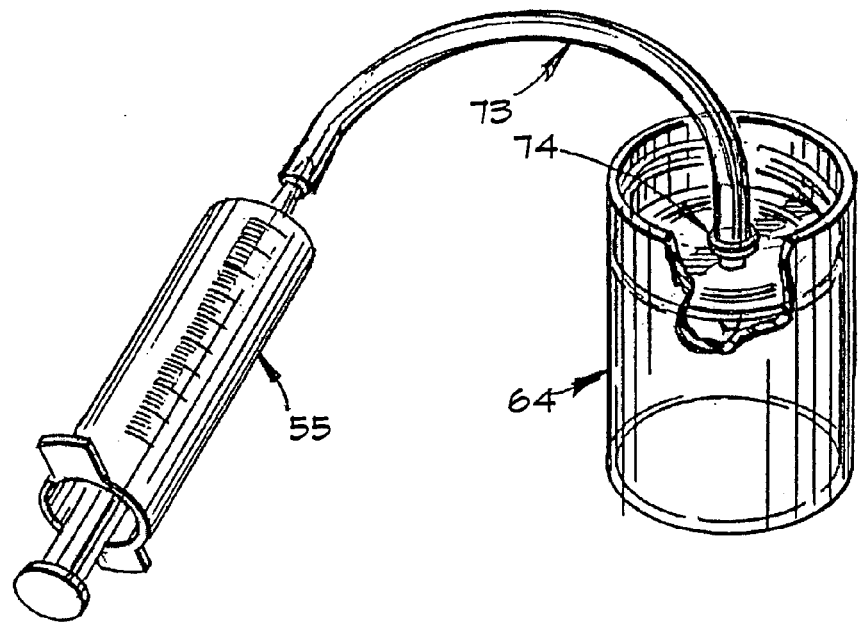
FIG. 2F
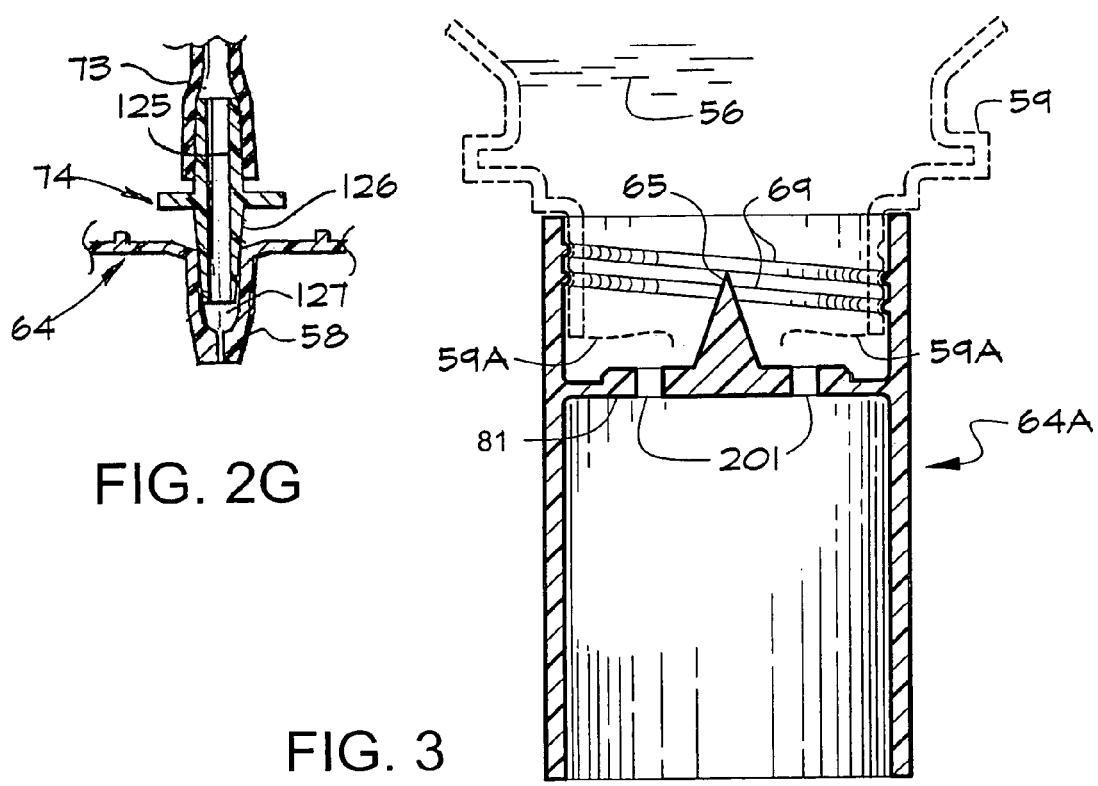
FIG. 2G
FIG. 3

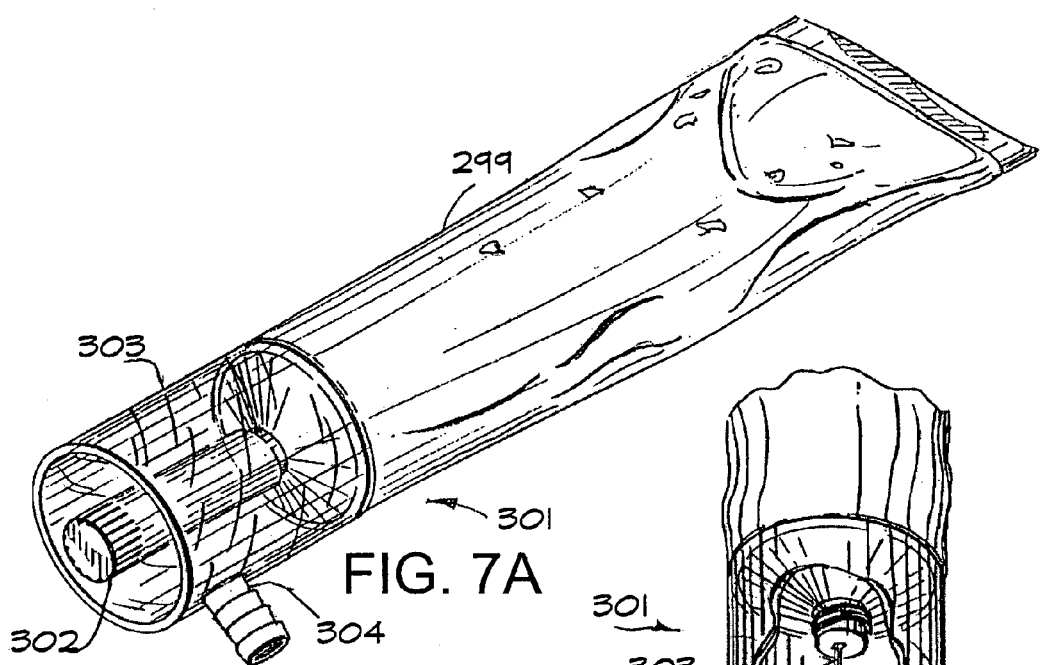
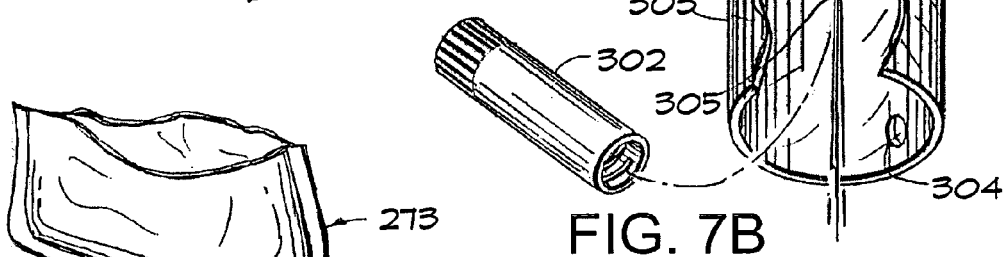
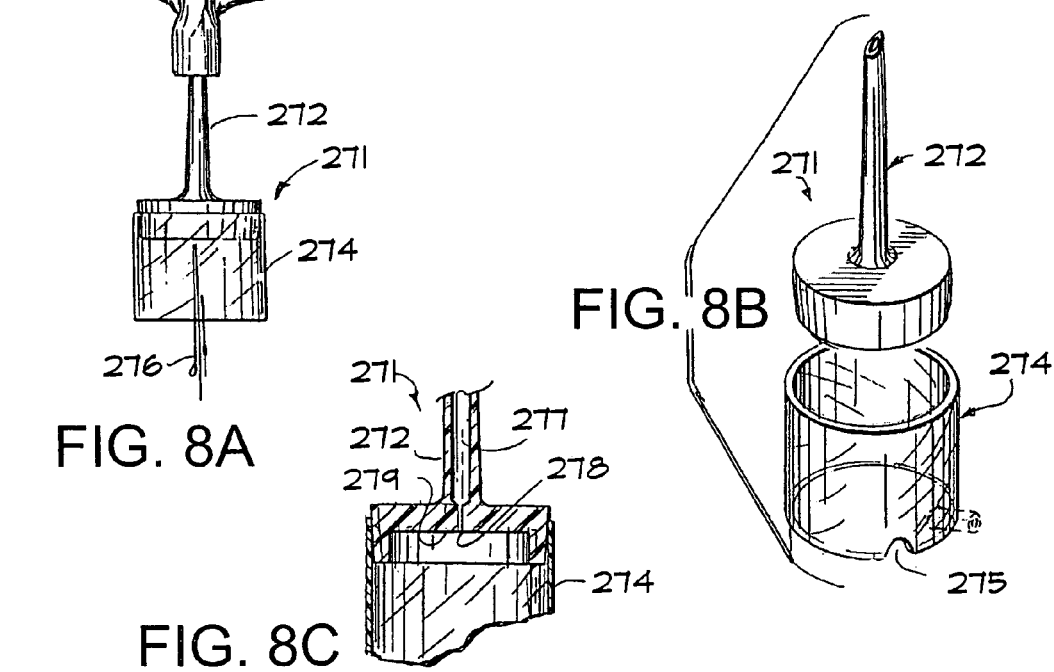

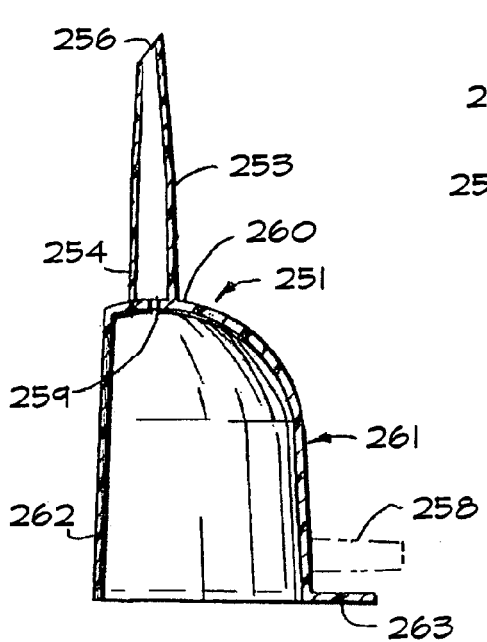
FIG. 10C
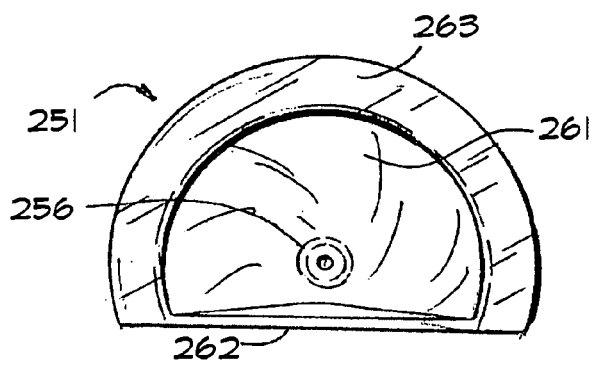
FIG. 10D
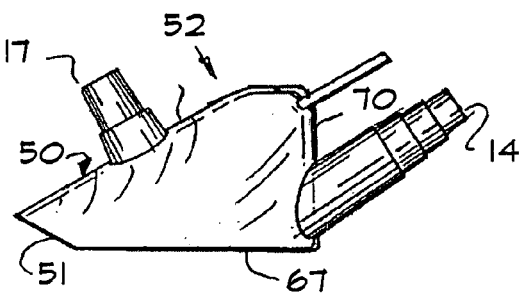
FIG. 11A
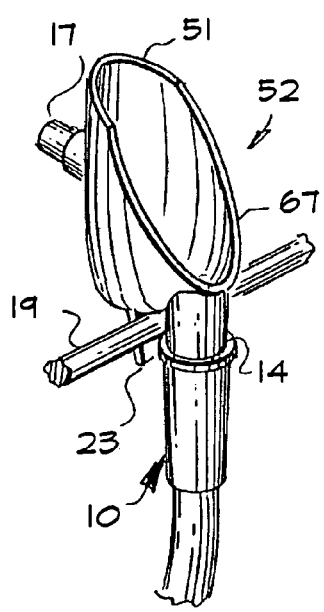
FIG. 11C
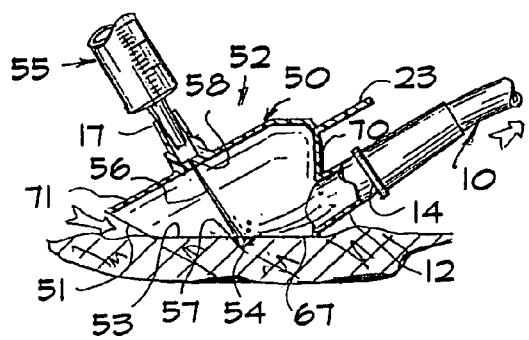
FIG. 11B
FIG. 11D

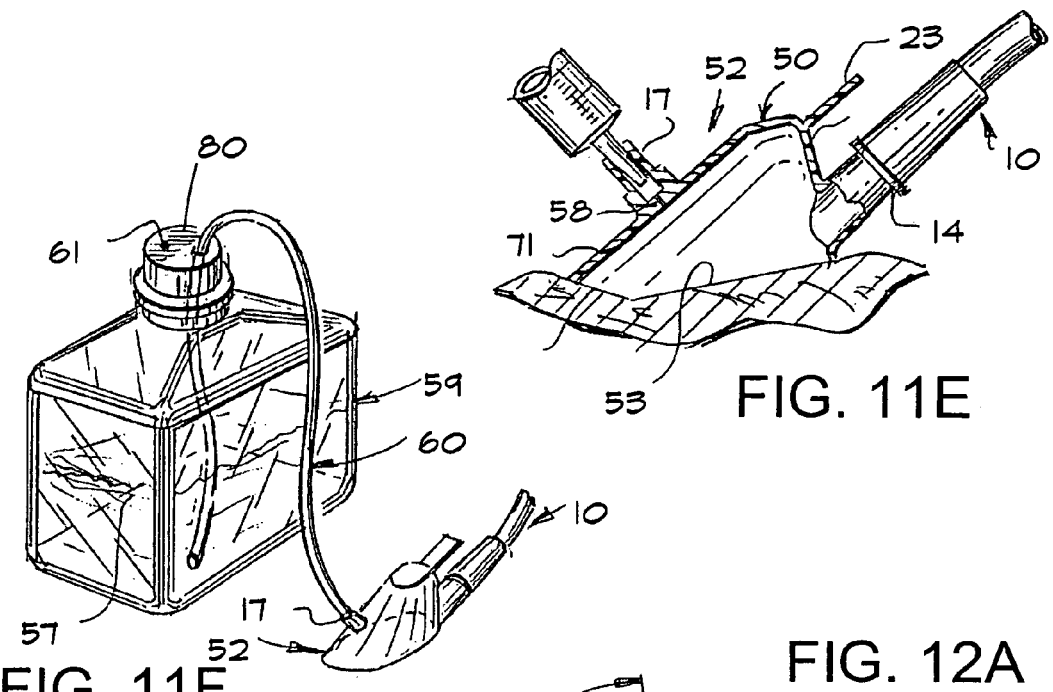
FIG. 11E
FIG. 11F
FIG. 12A
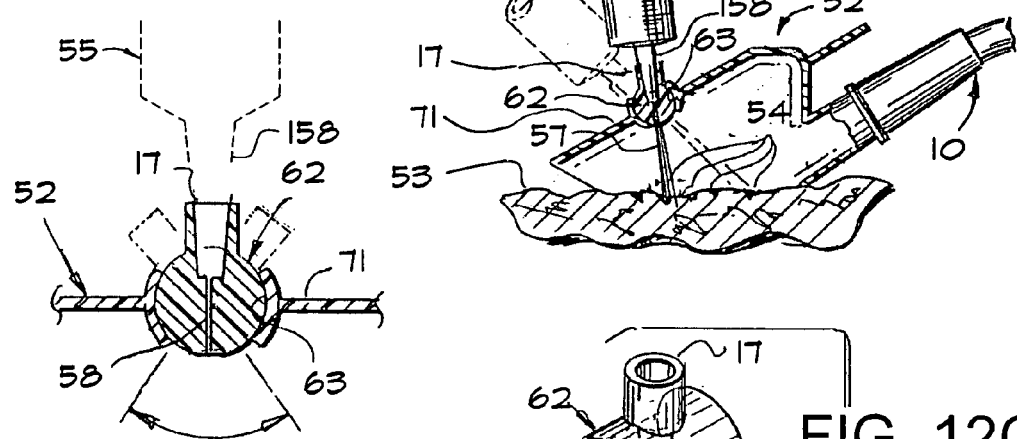
FIG. 12B
FIG. 12C
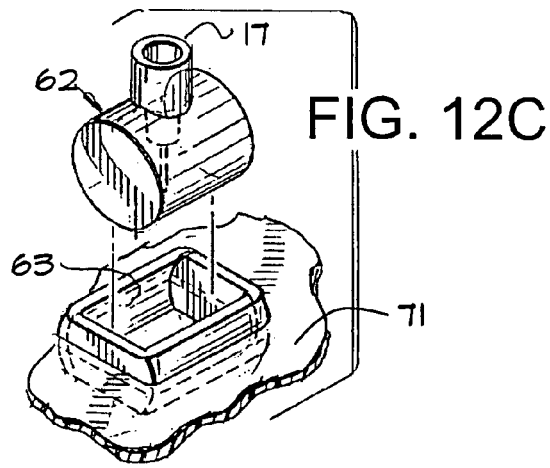

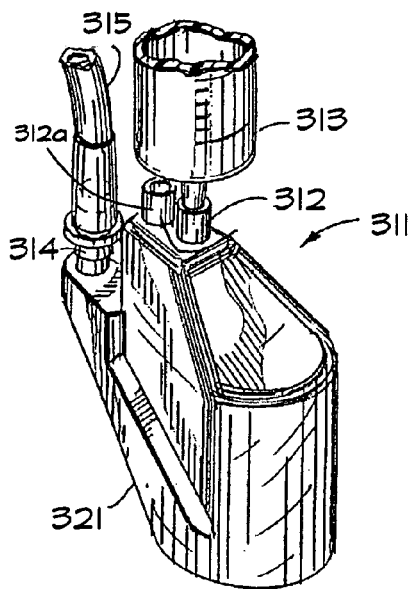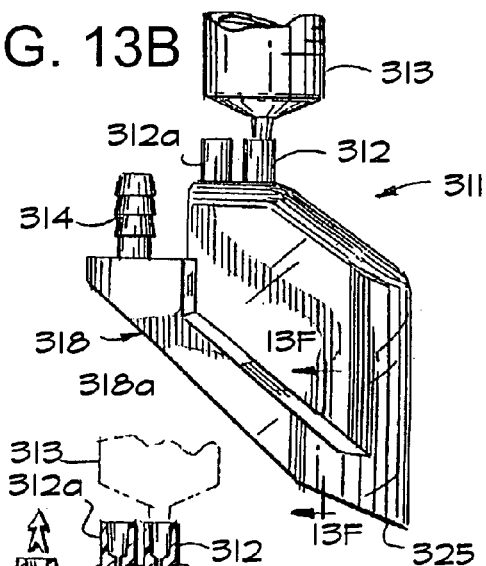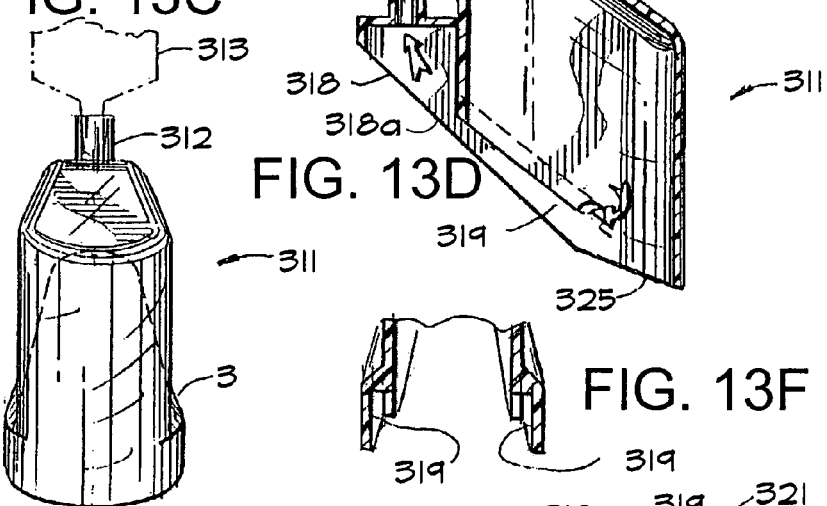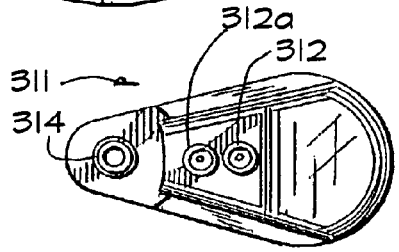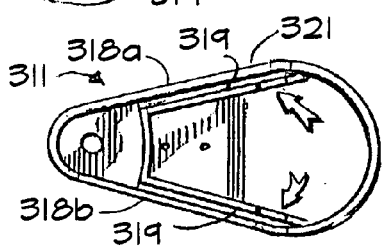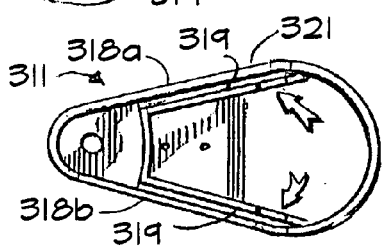
FIG. 13A
FIG. 13B
FIG. 13C
FIG. 13D
FIG. 13E
FIG. 13F
FIG. 13G

SPLASH SHIELD SYSTEM

CROSS-REFERENCE TO RELATED APPLICATIONS

The present application is a continuation-in-part of related U.S. utility patent application Ser. No. 10/245,241, filed Sep. 17, 2002, entitled "SPLASH SHIELD SYSTEM", which is a continuation-in-part of U.S. utility patent application Ser. No. 10/123,966, filed Apr. 16, 2002, entitled "MEDICAL COMPONENT SYSTEM", which is a continuation-in-part of related U.S. utility patent application Ser. No. 09/484,666, filed Jan. 18, 2000 now abandoned, entitled "MEDICAL COMPONENT SYSTEM", now abandoned, which are incorporated herein by this reference, and which are not admitted to be prior art with respect to the present invention by the mention in this cross-reference section.

BACKGROUND

This invention relates to providing a medical system assisting more efficient and safer performance of medical procedures. More particularly, this invention concerns a medical system comprising apparatus and methods for improved irrigation and lavage. With respect to irrigation problems, when a patient has a wound, it is desirable to irrigate the wound with a solution such as normal saline. Presumably the dilution effect of the irrigation will wash out bacteria and debris and prevent wound contamination, infection and scarring. The more fluid, the greater the degree of success in prevention. A higher pressure of irrigation could also help remove bacteria and push out unwanted debris. Unfortunately, when using large volumes or high amounts of pressures, there is a high likelihood of contaminated fluid spreading to unwanted surfaces, including splashing onto a health care provider or drenching the patient. This is undesirable as the risk of spreading of disease is heightened and there are undesirable effects of getting a patient wet (for example, a trauma patient with multiple wounds might be hypothermic from a large amount of irrigation fluid evaporating on his body, or a child with a facial laceration might become hypothermic from the excess fluid wetting its clothing during the winter). The excess fluid will also soil laundry and require increased housekeeping services, using existing methods of irrigation. This is also an inconvenience for otherwise healthy patients. They may have to remove their clothing to prevent them from getting soaked. This may be uncomfortable for the patient in a busy emergency room; and the time necessary for the patient to disrobe would delay a doctor's or nurse's ability to treat such patient or other waiting patients more expeditiously. These disadvantages will decrease the incentive for an operator, such as a physician, to appropriately use optimal large volumes of irrigation fluid; and therefore the risk of wound complications will increase.

Wound irrigation shields with a circular flat surface are non-conforming to most body surfaces that sustain lacerations, since the more commonly lacerated surfaces are on an edge or ridge or prominence rather than a flat surface (e.g., portions of arms or fingers, etc.). So use of such shields typically leaves open gaps where fluid can spray out and contaminate the nearby regions. Since the flat base surface of such devices can only be used in one plane when the base is placed with stability against the skin for support, a user is encouraged to use only the perpendicular-to-the-skin spray orientation that the device provides, rather than angling the device in non-perpendicular orientations. It is noted, and it is an object and feature of this invention, that angling the spray would allow visualization from directly above—where the operator is most likely going to be looking from and where his/her viewpoint is more likely to be.

Another problem with a generally perpendicular angle of an irrigation jet is that this configuration tends to push wound bacteria or debris straight down and deeper into the wound. As an object and feature of this invention, angling the irrigation jet gives a horizontal vector to the forces on the bacteria and debris within the wound and this tends to push the debris out of the wound rather than just farther into it. It could push the debris out of a wound by sometimes aiming the flow underneath the target and thus pushing it up by the upwelling of the irrigation fluid rather than jamming it farther in.

Nor does the prior art (in using such "perpendicular" splash shields) teach efficient removal of large amounts of irrigating fluid. Typically, at present, workers must mop up the blood-tinged irrigation fluids with sheets and towels, with associated increased hospital wastes and costs and increased biohazard risks to hospital personnel, including risk of slipping on a wet floor, for example. If a wound irrigation shield has a suction irrigation-removal system has a suction coaxially placed with the irrigation unit, this will distort the irrigation stream; in fact, if the forces of the stream are small and the vacuum of the removal system is great, there may not be enough force for the stream to reach the wound. Further, if the removal outlet is high above the surface of the patient, it is less effective in suctioning fluid on a patient's body surface since it would have to have a strong vacuum to pull the irrigation fluid off the body up into the air and into the vacuum outlet. Thus it would be beneficial, and it is an object and feature of this invention to provide a more efficient system and means for wound irrigation and irrigating-fluid removal.

Further objects and features of my invention are not taught in the prior art. There is no teaching of a wound splash shield device with an irrigation fluid jet that can be activated by suctioning or siphoning that provides an automatic irrigation stream that can deliver high volumes of irrigation; nor is there any teaching of a wound splash shield device with an irrigation fluid jet that can be activated by suctioning or siphoning that requires fluid to traverse a wound before reaching an outlet that provides an automatic irrigation stream that can deliver high volumes of irrigation fluid to cleanse the wound with minimal effort and also providing an effective removal means of this irrigation fluid. Nor is there teaching of this fluid, once activated, having a continual non-automatic stream powered by a continued suctioning or siphoning effect; nor is there teaching of such a device also having a flexible catheter attached to an inlet for suctioning or siphoning or such a device also being capable of accommodating a more active irrigation fluid delivery device such as a syringe to the same port or another port to enable one device to be capable of a variety of irrigation delivery techniques.

As most wounds are linear (or a combination of linear openings in the skin), the rounded lateral surfaces are generally wasted space that, as mentioned above, can actually be detrimental to optimal performance. There is no teaching in prior art of wound splash shields, as in a feature of my inventions, with a more elongated opening or base, which would be better suited for most wound surfaces, to economize space and prevent the outpouring or spraying of debris and contaminated fluid. Nor is there teaching in prior art of wound splash shields with a contoured opening or base that would be better suited for most wound surfaces on body prominences to perform a better effective seal to improve the activation or operation of a suction- or siphon-controlled splash shield.

In addition, when an operator empties a syringe using the described prior art splash shield, the operator must actively detach the shield from the syringe. This active step is one more that will discourage a user who, for example, is in a busy emergency room, from using the optimal large volume of irrigation fluid.

Nor does the prior art teach, as provided in a feature of my invention, a method of controllably causing a stable angled flow down a linear space. And there is no teaching, as provided in my invention, of a construction permitting and enhancing that an angled flow of a device can be rocked back and forth for providing an effective angular irrigation stream. Another disadvantage of a perpendicularly angled stream is that the force, when in using a plunger device, is pressing down directly on the skin. In general, there are no lateral forces in a consistent direction that would ease the movement of the device from one region of a wound to another, particularly in a linear wound. Another drawback of the prior art is that there is no teaching of a vent or relief feature (as in my instant invention), for more safe and efficient suction of excess irrigation fluid; and there is no teaching of such a device with a suction-powered removal system with a vent or relief feature that would prevent a full suction from occurring when the device's base forms a firm seal against a body surface. Such a suction force without a relief feature could pull the skin up into the device and cause damage and deformity to what might already be injured tissue.

Further, one standard type of container of sterile fluid (such as saline) in medicine is an "IV bag", which may contain sterile normal saline solution. The IV bags are compressible and therefore one could propel fluid through the outlet and onto a wound. But prior devices using IV bags for irrigation suffer the lack (provided as a feature of my present invention) of a barrier to restrain splashed fluid. Such barriers are more and more generally used in medicine due to the risk of blood-borne disease such as HIV. And using connectors between such devices has numerous limitations. Assembling the devices together by the available friction fits requires time. Multiple separate devices might need to be unloaded out of sterile containers, resulting in increased time for the procedure, increased waste of packaging, increased cost of packaging and increased risk of the parts or the users breaking sterile protocols. In addition, vigilance during the procedure is required to assure that the devices do not disconnect. If such a disconnect occurred during a procedure unexpectedly, this would lead to a dangerous situation where a clinician might be exposed to a patient's bodily fluids and or where fluid might drench a patient or hospital room. This problem of disconnecting may be particularly a problem with the use of a compressible IV bag, as the act of manual compression requires a significant amount of force and might leave a user's hands shaky and unstable causing the assembled unit to be moved around quite a bit, possibly separating the unit apart.

Another limitation of the prior art is that the devices that do have splash shields have only one aperture for injection and therefore allow for only one size of jet stream. It is common to have many user preferences in wound irrigation. Some might prefer a quicker, lower-pressure higher-volume large-aperture injection and others might prefer a slower, higher-pressure lower-volume narrower-aperture injection. Prior art devices only allow for one type of injection stream through a single aperture. Or such devices can accept different IV catheter hub and tubing assemblies with different diameters to vary the pressure and flow; but this method requires additional assembly and the use of additional costly sterile packaging with disadvantages such as those described above. Others in the prior art use a single injection inlet with a complex mechanically powered water injection unit with a variable motor unit. This unit is costly and cumbersome and unlikely to be disposable. Its bulk makes it cumbersome for maneuvering on different parts of a patient's body. There is a lack of (as in my present invention) manually operated wound irrigation shields and injectors that have an inlet mechanism that allows for simple variation of injection flow to easily accommodate for user preferences. Such a device is needed and would gain broader acceptance and use; and it would reduce the stocking of multiple models or parts and would eliminate the need for assembly of connectors. Nor do any of these (as in my present invention for eliminating the problems set forth in this paragraph) have such a mechanism using IV spikes as connector inlets. Nor do any of these have a mechanism using an IV spike as a connector and having grooves or protrusions for stabilizing the interface between the squeeze bag or tube such as an IV bag and the shielding device. Nor do they have any means for improving the gripping means, or providing a flat surface for pivoting the injection stream. Nor do any of these have such a mechanism using a single part with an irrigation shield. Nor do any of these mechanisms have connectors that fit inside the already standardized fluid container outlets. Current wound irrigation shields fit over the fluid container outlets of the device; and the increased diameter increases the visual obstruction caused by the connection. Even minor increases in diameter can be of significance for wound irrigation shields that are small relative to the size of the fluid container which may already be causing a visual obstruction.

In the area of wound irrigation, the current art of syringes requires that one use a syringe with a limited volume multiple times to draw up irrigation fluid and then expel it. If a larger volume syringe is desired to reduce the time-consuming and cumbersome steps of drawing up fluid and expelling it, the syringe diameter is limited by the size of an irrigation container opening. As previously described, re-sealable irrigation containers, such as bottles, are preferable to open basins or baths. It is also desirable to have a single hand operated syringe so a second hand may be stabilizing other equipment such as a splash shield. Prior art limits the dimension of a single hand operated syringe used in an irrigation procedure with a re-sealable irrigation fluid container to be of a dimension with a barrel width narrower than the irrigation fluid container and a length less than a single hand span. Current art does not teach having a larger volume syringe for this purpose, or more specifically having a longer single hand operated syringe with a simple plunger delivery of the reservoir contents.

Another disadvantage of the prior art in the delivery of contents is the delivery of contents that require a higher pressure to deliver. Examples are fluids such as normal saline that is pushed through a small aperture under high pressure for improved irrigation results, or high viscosity fluids, including a slurry of activated charcoal to be delivered through a tube to a patient with an overdose. As syringes are hand operated, when a hand, including a fully extended thumb and gripping fingers are extended and intended to contract to operate the syringe, it is in a less stable position than in a less than extended or contracted position. It is therefore desirable to have a syringe that reduces the instability of a hand operated syringe delivering contents under high pressure when the plunger is an extended (including fully extended) position. Unfortunately, the prior art does not address this need adequately, and syringes that require high pressure often require two hands for operation to maintain stability—or possibly require the device to be placed against the body. If one attempts at addressing this concern by having improved gripping means on the barrel of the syringe and at the end of the syringe plunger, when the syringe is in a fully extended position, the system is still relatively unstable, especially when high pressure is necessary to hand operate the device. Additionally, if the syringe were of a length greater than one hand length, the syringe could not be operated by one hand and would therefore require more manipulations to operate.

OBJECTS AND FEATURES OF THE INVENTION

A primary object and feature of the present invention is to fulfill the above-mentioned needs by the provision of an improved splash shield system. A further primary object and feature of this invention is to provide a splash shield system which provides a horizontal vector to the forces of the irrigation fluid on the wound. Another primary object and feature of this invention is to provide a splash shield system which easily accommodates connection to a variety of different sources of irrigation fluid. Another primary object and feature of the present invention is to provide such a splash shield system which is efficient, inexpensive, and handy. Another primary object and feature of the present invention is to provide such a splash shield system which can be easily manipulated by the user to direct the irrigation fluid to different locations. Other objects and features of this invention will become apparent with reference to the following specification and claims.

SUMMARY OF THE INVENTION

In accordance with a preferred embodiment hereof, this invention provides a splash shield system for irrigation of a patient's wound and suction removal of excess irrigation fluid, comprising: a body structured and arranged to contain irrigation fluid, wherein such body has a maximum height dimension, and an input opening structured and arranged to allow the irrigation fluid into such body, wherein such input opening is located at a substantially lower position than such maximum height dimension. Moreover, it provides such a splash shield system further comprising: an output opening structured and arranged to allow suctioning excess irrigation fluid from within such body; wherein such output opening is structured and arranged to draw excess irrigation fluid from such body toward a location approximately at a position symmetrically opposed (with respect to such maximum height dimension) from the location of such input opening. Additionally, it provides such a splash shield system wherein: a bottom peripheral circumference of such body has an oval-like shape. Also, it provides such a splash shield system wherein such input opening comprises: a swivel structured and arranged to allow a user to direct a stream of irrigation fluid to selected portions of the skin of a patient; wherein such swivel comprises an attacher structured and arranged to allow attachment of a source of irrigation fluid to such swivel. In addition, it provides such a splash shield system wherein such output opening further comprises: an output nozzle structured and arranged to attach to a vacuum line; a conduit structured and arranged to direct suction flow across such splash portion toward such output nozzle; wherein such conduit comprises at least one channel along a periphery of such body extending from such output nozzle to a location approximately at a position symmetrically opposed from the location of such input opening. And, it provides such a splash shield system further comprising an irrigation-source connector structured and arranged to connect such input opening to a source of irrigation fluid; wherein such irrigation-source connector is structured and arranged to allow a luer connection. Further, it provides such a splash shield system wherein such input opening is structured and arranged to assist in directing irrigation fluid at an oblique angle from vertical.

Additionally, in accordance with a preferred embodiment hereof, this invention provides a splash shield system for protecting a user from contact with irrigation fluid directed at a patient's wound comprising: a body; having a first end and a second end, and a cylindrical exterior wall an irrigation-source connector structured and arranged to connect such body, at such first end, to a source of irrigation fluid; wherein such body comprises at least one inner hollow; wherein such second end, is open to such at least one inner hollow; wherein such splash shield system is structured and arranged in such manner as to protect the user from contact with the irrigation fluid. Even further, it provides such a splash shield system wherein such cylindrical exterior wall is substantially round; and such at least one inner hollow comprises a substantially round cylinder. Moreover, it provides such a splash shield system further comprising a source of irrigation fluid connected to such body at a such first end of such body. Additionally, it provides such a splash shield system further comprising an adapter structured and arranged to allow a connection between such body and such source of irrigation fluid. Also, it provides such a splash shield system wherein such adapter allows connection of such body to multiple varieties of such source of irrigation fluid. In addition, it provides such a splash shield system wherein such adapter comprises a nozzle structured and arranged to direct a narrow stream of the irrigation fluid towards the wound. And, it provides such a splash shield system wherein such adapter comprises threads structured and arranged to provide a threaded connection with the source of irrigation fluid. Further, it provides such a splash shield system wherein such threads comprise internal threads structured and arranged to connect with external threads on a neck of a irrigation fluid bottle. Even further, it provides such a splash shield system further comprising: a bottle structured and arranged to contain irrigation fluid, such bottle comprising, a neck, wherein such neck comprises external threads structured and arranged to connect with a bottle cap. Moreover, it provides such a splash shield system further comprising: at least one end cap wherein such at least one end cap comprises a cap portion structured and arranged to close at least one end of such body. Additionally, it provides such a splash shield system wherein such at least one end cap covers and seals at least one end of such body in such manner as to protect internal sterility of such body. Also, it provides such a splash shield system wherein at least one such end cap portion of a such end cap comprises an externally-open pocket extending into such hollow cylindrical portion of such end cap. In addition, it provides such a splash shield system wherein such adapter comprises an IV-spike connector.

Further, in accordance with a preferred embodiment hereof, this invention provides a splash shield system for protecting a user from contact with irrigation fluid directed at a patient's wound comprising: a body, having a first end and a second end wherein such first end is open to a first hollow portion of such body and such second end is open to a second hollow portion of such body; an irrigation-source connecter structured and arranged to connect such body, adjacent the first end, to a source of irrigation fluid; a partition, between such first hollow portion and such second hollow portion, [at least about the area of an irrigation bottle-neck]; wherein such partition comprises at least one nozzle structured and arranged to direct at least one narrow stream of the irrigation fluid towards the wound; wherein such splash shield system is structured and arranged in such manner as to protect the user from contact with the irrigation fluid. And, it provides such a splash shield system wherein such partition further comprises, at least one hole through such partition (in addition to such nozzle). Further, it provides such a splash shield system wherein such irrigation-source connecter comprises threads structured and arranged to provide a threaded connection. Even further, it provides such a splash shield system wherein such threads comprise helical threads. Moreover, it provides such a splash shield system wherein such irrigation-source connecter further comprises at least one adapter structured and arranged to provide a connection to a syringe tip.

Also, in accordance with a preferred embodiment hereof, this invention provides a splash shield system for protecting a user from contact with irrigation fluid directed at a patient's wound comprising: a body structured and arranged to assist in protecting a user from contact with irrigation fluid directed at a patient's wound; an irrigation-source connecter structured and arranged to connect such body, at a first end of such body, to a source of irrigation fluid; wherein such irrigation-source connecter comprises a puncturer structured and arranged to puncture at least one barrier between such body and the source of irrigation fluid. Additionally, it provides such a splash shield system wherein such puncturer comprises a spike. Also, it provides such a splash shield system wherein such spike comprises at least one opening structured and arranged to transport the irrigation fluid from the source of irrigation fluid to such body. In addition, it provides such a splash shield system wherein such spike comprises an IV-spike connecter, unitary with such body.

Additionally, in accordance with a preferred embodiment hereof, this invention provides a splash shield system for protecting a user from contact with irrigation fluid directed at a patient's wound comprising: a transparent body structured and arranged to assist in protecting a user from contact with irrigation fluid directed at a patient's wound; an irrigation-source connecter structured and arranged to connect such body, at a first end of such body, to a source of irrigation fluid; wherein such transparent body comprises at least one bottom opening wherein a bottom periphery of such at least one bottom opening is substantially non-planar. Also, it provides such a splash shield system wherein such bottom peripheral circumference is structured and arranged to allow rocking such body. And, it provides such a splash shield system wherein such bottom peripheral circumference is saddle-shaped.

Additionally, in accordance with a preferred embodiment hereof, this invention provides a splash shield system comprising: a transparent body structured and arranged to assist in protecting a user from contact with irrigation fluid directed at a patient's wound; an irrigation-source connecter structured and arranged to connect such body to a source of irrigation fluid; wherein such body includes at least one bottom opening; wherein the ratio of a maximum length of such at least one bottom opening compared to a maximum width of such at least one bottom opening is at least 1.5:1.0.

BRIEF DESCRIPTION OF DRAWINGS

FIG. 2F is a perspective view illustrating the use of the splash shield of FIG. 1 using a syringe with connecting tubing and an adapter.

FIG. 2G is a sectional view of the adapter connection area of the embodiment of FIG. 2F illustrating the area detail.

FIG. 3 is a sectional view of another preferred embodiment of a splash shield according to the present invention, showing a puncturing means for breaking the seal on a source of irrigation fluid.

FIG. 7A is a perspective view of a preferred embodiment of a combined splash shield and irrigation squeeze tube according to the present invention.

FIG. 7B is a partial perspective view of the embodiment of FIG. 7A, partially cut away to show its use with cap removed.

FIG. 8A is front view illustrating yet another preferred embodiment of a splash shield according to the present invention, showing a spike connector attached to a squeeze bag and also fitted into a cylindrical splash shield element.

FIG. 8B is a perspective view of the embodiment of FIG. 8A, showing the spike connector separated from the cylindrical splash shield element.

FIG. 8C is a partial sectional view showing the connection details with the spike connector attached to the cylindrical splash shield element.

FIG. 10C is sectional side view of the embodiment of FIG. 10A illustrating the structural details thereof.

FIG. 10D is a bottom view of the embodiment of FIG. 10A.

FIG. 11A is a side elevation view of a preferred embodiment of the splash shield medical device of the present invention.

FIG. 11B is a top plan view of the embodiment of FIG. 11A.

FIG. 11C is a perspective view of the embodiment of FIG. 11A showing it in a restrained position.

FIG. 11D is a side sectional view of the embodiment of FIG. 11A, illustrating its operation.

FIG. 11E is a side sectional view of the embodiment of FIG. 11A, further illustrating operation with relief closure.

FIG. 11F is a perspective view of a preferred alternate usage of the splash shield of the type of FIG. 11A, further illustrating siphoning of irrigation fluid from a fluid container.

FIG. 12A is a side sectional view of an alternate preferred embodiment of the splash shield of the present invention, illustrating its operation incorporating an inlet swivel structure.

FIG. 12B is a partial expanded sectional view of the embodiment of FIG. 12A, illustrating swivel detail.

FIG. 12C is an exploded perspective view further illustrating the swivel detail of the embodiment of FIG. 12A.

FIG. 13A is a perspective view of yet another preferred embodiment of a splash shield according to the present invention, shown with an inlet attached to an irrigation syringe and an outlet attached to a vacuum line.

FIG. 13B is a side view of the embodiment of FIG. 13A, shown attached to the irrigation syringe.

FIG. 13C is a front view of the embodiment of FIG. 13A, with the irrigation syringe in dotted lines.

FIG. 13D is a side sectional view of the embodiment of FIG. 13A showing the structural details and fluid flow directions.

FIG. 13E is a top view of the embodiment of FIG. 13A.

FIG. 13F is a partial sectional view through the section 13F-47F of FIG. 13B.

FIG. 13G is a bottom view of the embodiment of FIG. 13A.

FIG. 14b is a top view of the embodiment of FIG. 14a.

FIG. 14c is sectional view of the embodiment of FIG. 14a.

DETAILED DESCRIPTION OF THE INVENTION

Figure 1:
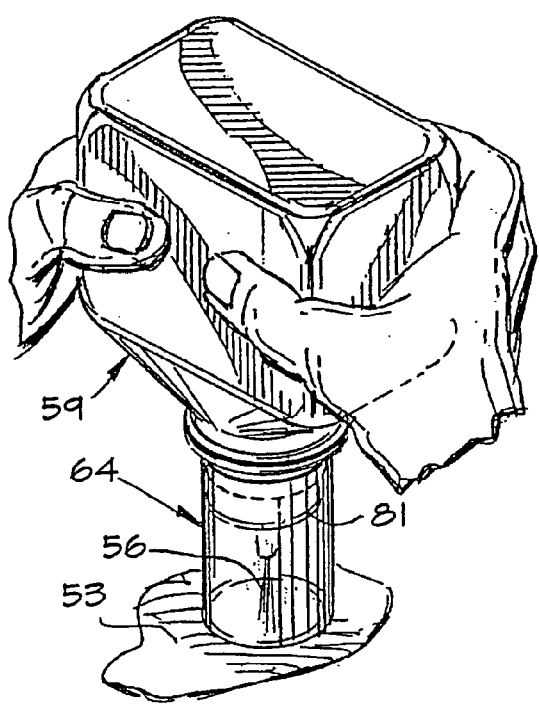
FIG. 1 is a perspective view of a preferred embodiment of a splash shield system according to the present invention, and showing use with an irrigation squeeze bottle.

FIG. 1 is a perspective view of a preferred embodiment of a splash shield system according to the present invention, showing use of splash shield 64 attached to wide mouth irrigation squeeze bottle 59. Preferably, wide mouth irrigation squeeze bottle 59 comprises a standard high volume plastic squeeze bottle of sterile fluid, as shown. Preferably, wide mouth irrigation squeeze bottle 59 comprises a volume of at least about 250 cc. Preferably, wide mouth irrigation squeeze bottle 59 comprises a volume less than about 1750 cc. Preferably, wide mouth irrigation squeeze bottle 59 comprises bottle neck finish portion 30, as shown. Preferably, bottle neck finish portion 30 comprises an inner diameter between about ¾ inches and about 1½ inches, most preferably between about ⅘ inches and about 1¼ inches. Preferably, bottle neck finish portion 30 comprises an outer diameter between about ⅘ inches and about 1¾ inches. Preferably, wide mouth irrigation squeeze bottle 59 comprises a standard wide mouth wound irrigation squeeze bottle, such as, for example, wide mouth wound irrigation squeeze bottles manufactured by BAXTER™, ABBOT™, or MCGAW™. Preferably, when wide mouth irrigation squeeze bottle 59 is squeezed, fluid 56 is squirted onto flesh 53 of the patient, as shown.

Figure 2B:
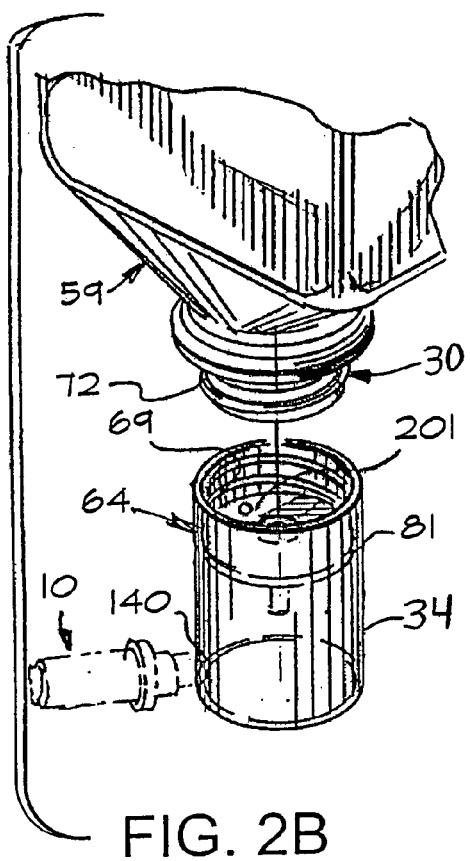
FIG. 2B is an exploded perspective view of the embodiment of FIG. 1, and further showing (in dotted lines) the structure of another preferred alternate embodiment using vacuum evacuation of irrigation fluid through a port situated near the plane of irrigation.
Figure 2C:
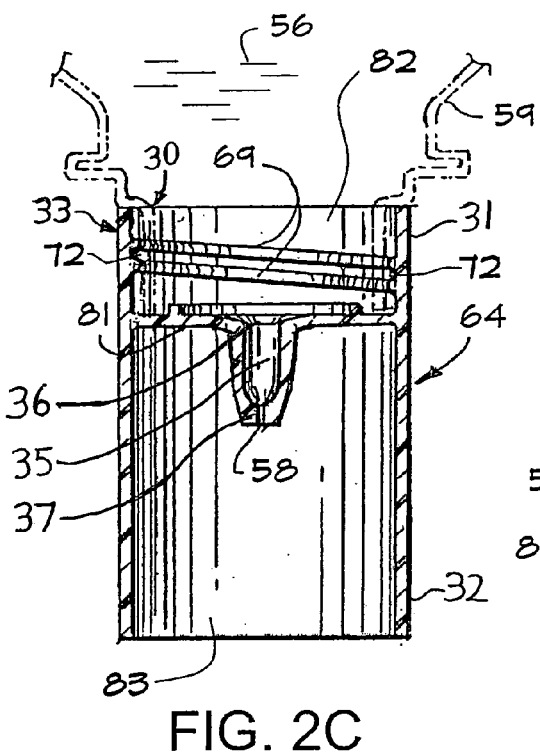
FIG. 2C is a sectional view of the embodiment of FIG. 1, illustrating details of preferred structure.

FIG. 2B shows a preferred embodiment of the present invention with wide mouth irrigation squeeze bottle 59 detached from splash shield 64. FIG. 2C is a sectional view of the embodiment of FIG. 1, illustrating details of a preferred structure. Preferably, splash shield 64 is transparent, as shown. Preferably, splash shield 64 comprises first end 31 and second end 32, as shown. Preferably, partition 81 divides first end 31 from second end 32, as shown. Preferably first end 31 comprises irrigation-source connector 33, as shown. Preferably, irrigation-source connector 33 comprises an inner diameter between about ⅘ inches and about 1¾ inches, most preferably between about 1.4 inches and about 1.6 inches. Preferably splash shield 64, including irrigation-source connector 33, partition 81, and inner hollow 83, consist of one monolithic piece. Preferably splash shield 64 is sterile.

Preferably, irrigation-source connector 33 comprises threads 69, as shown. Preferably, threads 69 comprise helical threads, as shown. Preferably second end 32 comprises inner hollow 83 as shown. Preferably, bottle neck finish portion 30 of wide mouth irrigation squeeze bottle 59 comprises threads 72, as shown. Preferably, threads 72 comprise male threads, as shown. Preferably, threads 72 comprise helical threads, as shown (embodying herein a bottle structured and arranged to contain irrigation fluid, such bottle comprising, a neck, wherein such neck comprises external threads structured and arranged to connect with a bottle cap) structured and arranged to couple with threads 69 (such threads embodying herein threads structured and arranged to provide a threaded connection with the source of irrigation fluid; and further embodying herein wherein such threads comprise internal threads structured and arranged to connect with external threads on a neck of a irrigation fluid bottle; and further embodying wherein such irrigation-source connecter comprises threads structured and arranged to provide a threaded connection; and further embodying herein an adapter structured and arranged to allow a connection between such body and such source of irrigation fluid) within inner hollow 82 of splash shield 64 to form a tight connection. Preferably, irrigation-source connector 33 is structured and arranged to connect to standard wide mouth wound irrigation squeeze bottles, such as, for example, those manufactured by BAXTER™, ABBOT™, or MCGAW™.

Upon reading the teachings of this specification, those with ordinary skill in the art will now understand that, under appropriate circumstances, considering such issues as cost of manufacture, compatibility, market demand, etc., other connection arrangements, such as, for example, non-helical threads, female threads, luer-type connections, non-threaded connections, snap on connections, etc., may suffice.

Preferably, partition 81 comprises orifice nozzle 58 for directing a stream of fluid from the irrigation source (such as, for example, wide mouth irrigation squeeze bottle 59) toward flesh 53 (embodying herein a body, having a first end and a second end wherein such first end is open to a first hollow portion of such body and such second end is open to a second hollow portion of such body; an irrigation-source connecter structured and arranged to connect such body, adjacent the first end, to a source of irrigation fluid; a partition, between such first hollow portion and such second hollow portion; wherein such partition comprises at least one nozzle structured and arranged to direct at least one narrow stream of the irrigation fluid towards the wound; wherein such splash shield system is structured and arranged in such manner as to protect the user from contact with the irrigation fluid; and further embodying herein wherein such adapter comprises a nozzle structured and arranged to direct a narrow stream of the irrigation fluid towards the wound).

Preferably, nozzle 58 protrudes from partition 81, as shown. Preferably, nozzle 58 protrudes from partition 81 a distance between about 0.005 inches to about 1 inch, as shown. Preferably nozzle 58 comprises at least one passageway 35 with at least one cross-sectional area, that decreases from at least one inlet port 36 of said at least one nozzle to at least one outlet port 37 of said at least one nozzle, forming at least one venturi passageway 35, as shown. Preferably, the length of passageway 35 is between about 0.005 inches to about 1 inch.

Preferably, splash shield 64 comprises a cylindrical exterior wall portion 34 (see FIG. 2B), as shown, wherein "cylindrical", as used throughout this specification, is defined in the broad mathematical sense as a surface traced by a straight line moving parallel to a fixed straight line and intersecting a fixed planar closed curve. Preferably cylindrical exterior wall portion 34 is substantially round. Preferably inner hollow 83 comprises a substantially round cylindrical portion, as shown (embodying herein a body having a first end and a second end, and a cylindrical exterior wall and irrigation-source connector structured and arranged to connect such body, at such first end, to a source of irrigation fluid; wherein such body comprises at least one inner hollow; wherein such second end, is open to such at least one inner hollow; wherein such splash shield system is structured and arranged in such manner as to protect the user from contact with the irrigation fluid; and further embodying herein wherein such cylindrical exterior wall is substantially round; and such at least one inner hollow comprises a substantially round cylinder). Upon reading the teachings of this specification, those with ordinary skill in the art will now understand that, under appropriate circumstances, considering such issues as intended use, user preference, cost of manufacture, etc., other splash shield shape arrangements, such as, for example, non-cylindrical portions, conical shaped portions, asymmetrical shaped portions, etc., may suffice.

According to the preferred embodiment shown in FIG. 1, there is preferably a single nozzle for irrigating flesh 53 with fluid 56, as shown. According to the preferred embodiment shown in FIG. 2B, partition 81 preferably comprises at least one additional hole 201 to facilitate irrigating flesh 53 with multiple streams of fluid 56 (wherein such partition further comprises, at least one hole through such partition (in addition to such nozzle)). Thus, when bottle 59 is attached and squeezed, fluid 56 is forced into and through orifice nozzle 58 (and also, through hole 201), as shown.

FIG. 2B also shows (in dotted lines) the structure of another preferred alternate embodiment using vacuum evacuation of irrigation fluid by vacuum line 10 through a port 140 situated near (as shown) the plane of irrigation (embodying herein an output opening structured and arranged to allow suctioning excess irrigation fluid from within such body).

Figure 2D:
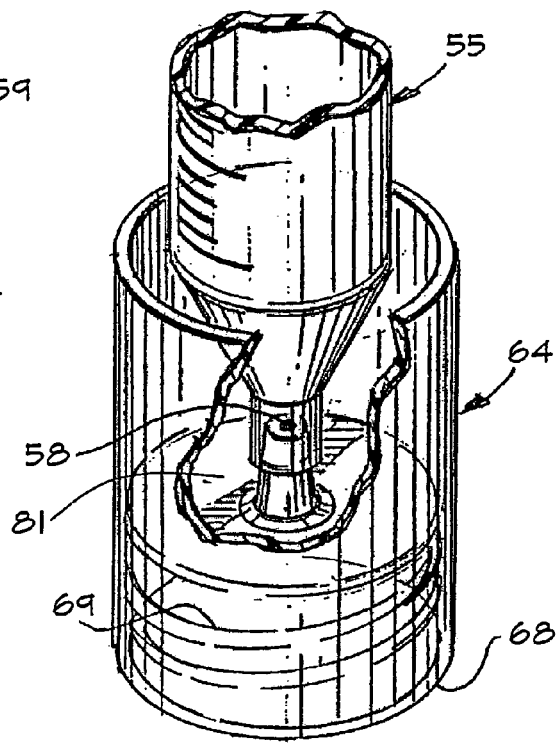
FIG. 2D is a perspective view illustrating the use of the splash shield of FIG. 1, inverted for use with a syringe.
Figure 2E:
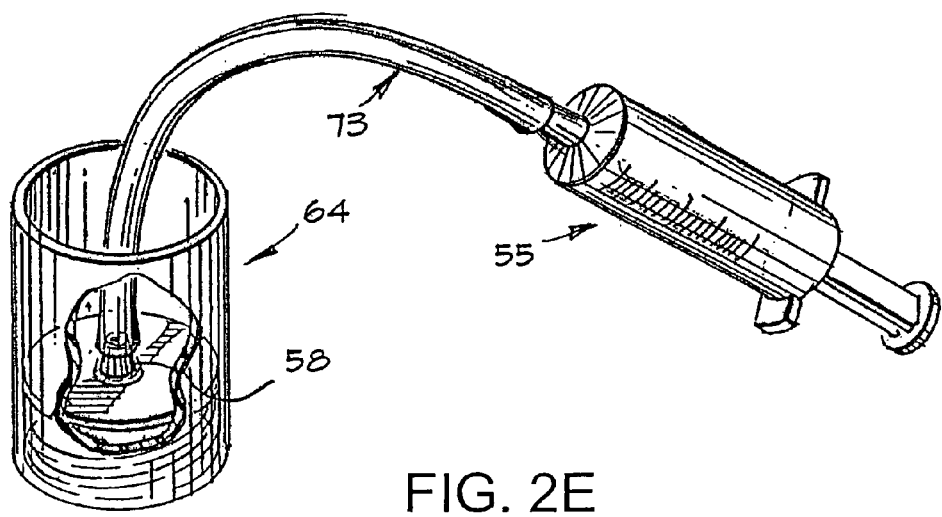
FIG. 2E is a perspective view illustrating the use of the splash shield of FIG. 2D using a syringe with connecting tubing.

FIG. 2D is a perspective view illustrating the use of the splash shield 64 of FIG. 1 inverted for use with a syringe 55. In this embodiment, the open unthreaded end of splash shield 64 receives a syringe 55 whose nozzle fits over the now protruding (from the former underside of partition 81) part of orifice nozzle 58, as shown. Thus, when syringe 55 discharges its fluid, the threaded portion 68 of splash shield 64 now acts as a splash shield. Similarly, FIG. 2E is a perspective view illustrating the use of the splash shield 64 "upside down" arrangement of FIG. 2D using a syringe 55 with connecting tubing 73, which tubing 73 is in this case connected over the protruding orifice nozzle 58.

FIG. 2F is a perspective view illustrating the use of the splash shield 64 of FIG. 1 using a syringe 55 with connecting tubing 73 and an adapter 74. FIG. 2G is a sectional view of the adapter 74 connection area of the embodiment of FIG. 2F illustrating the area detail. As shown, tubing 73 fits over an upper male portion 125 of the adapter 74 while a lower male portion 126 of the adapter 74 fits within the upper hollow 127 of orifice nozzle 58 (embodying herein wherein such adapter allows connection of such body to multiple varieties of such source of irrigation fluid). Preferably, upper hollow 127 also allows connection to an irrigation-source with a syringe tip (embodying herein wherein such irrigation-source connecter further comprises at least one adapter structured and arranged to provide a connection to a syringe tip).

FIG. 3 is a sectional view of yet another preferred embodiment of a splash shield 64A according to the present invention, meshed with an irrigation squeeze bottle 59, illustrating details of preferred structure. Preferably, splash shield 64A has a puncturer 65, as shown (embodying herein a body structured and arranged to assist in protecting a user from contact with irrigation fluid directed at a patient's wound; an irrigation-source connecter structured and arranged to connect such body, at a first end of such body, to a source of irrigation fluid; wherein such irrigation-source connecter comprises a puncturer structured and arranged to puncture at least one barrier between such body and the source of irrigation fluid and further embodying wherein such puncturer comprises a spike). As splash shield 64A is meshed with bottle 59, bottle membrane 59A (which acts as a barrier to fluid escaping the bottle 59) is punctured by puncturer 65, which permits fluid to exit from bottle 59. Below the threads 69 of splash shield 64A is internal partition 81 sealing the open/bottom end of splash shield 64A except for hole(s) 201. Preferably, puncturer 65 does not puncture bottle membrane 59A until after sufficient connection between the bottle 59 and the splash shield 64A is made to provide a sufficient seal preventing fluid from leaking from the meshed connection. Preferably, puncturer 65 punctures a bottle membrane 59A when the meshed connection between splash shield 64A and bottle 59 is already engaged, but not yet fully and completely seated, preferably when the meshed connection is approximately half-way complete. Thus, when bottle 59 is attached and squeezed, fluid 56 is forced into and through hole(s) 201.

Figure 4:
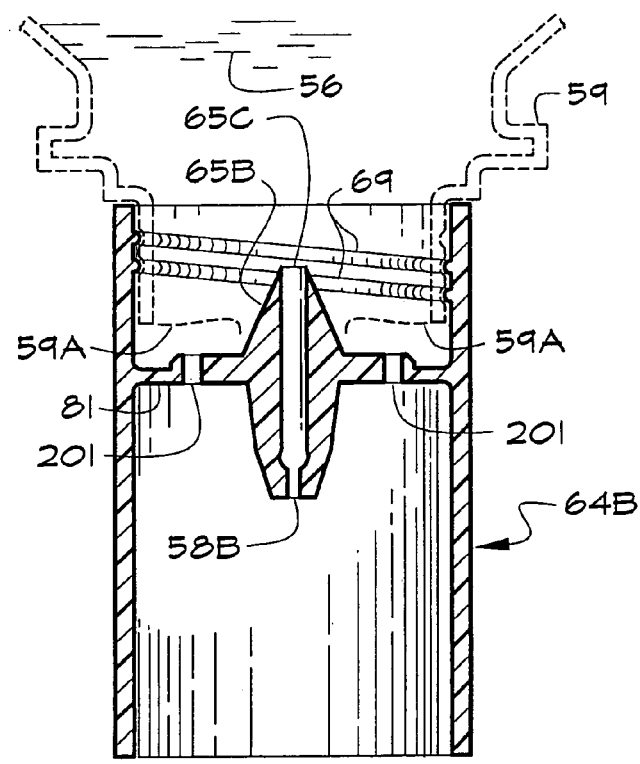
FIG. 4 is a sectional view of another preferred embodiment of a splash shield according to the present invention, showing a puncturing means with integral fluid transport means.

FIG. 4 is a sectional view of yet another preferred embodiment of a splash shield 64B according to the present invention, meshed with an irrigation squeeze bottle 59, illustrating details of preferred structure. Preferably, splash shield 64B has a puncturer 65B. As splash shield 64B is meshed with bottle 59, bottle membrane 59A is punctured by puncturer 65B, which permits fluid to exit from bottle 59. One or more fluid channel(s) 65C in puncturer 65B permits fluid 56 to exit from bottle 59 into orifice nozzle 58B (embodying herein wherein such spike comprises at least one opening structured and arranged to transport the irrigation fluid from the source of irrigation fluid to such body). Below the threads 69 of splash shield 64B is internal partition 81 sealing the open/bottom end of splash shield 64B except for orifice nozzle 58B for directing a stream toward flesh 53. It is noted, that one or more additional hole(s) 201 may be optionally found going through partition 81 in order to increase irrigation flow to a wound. Preferably, puncturer 65B does not puncture bottle membrane 59A until after sufficient connection between the bottle 59 and the splash shield 64B is made to provide a sufficient seal preventing fluid from leaking from the meshed connection. Preferably, puncturer 65B punctures bottle membrane 59A when the meshed connection between splash shield 64B and bottle 59 is already engaged, but not yet fully and completely seated, preferably when the meshed connection is approximately half-way complete. Thus, when bottle 59 is attached and squeezed, fluid 56 is forced through the fluid channel(s) 65C and through orifice nozzle 58 (and also, optionally, through optional hole(s) 201), as shown.

Figure 5A:
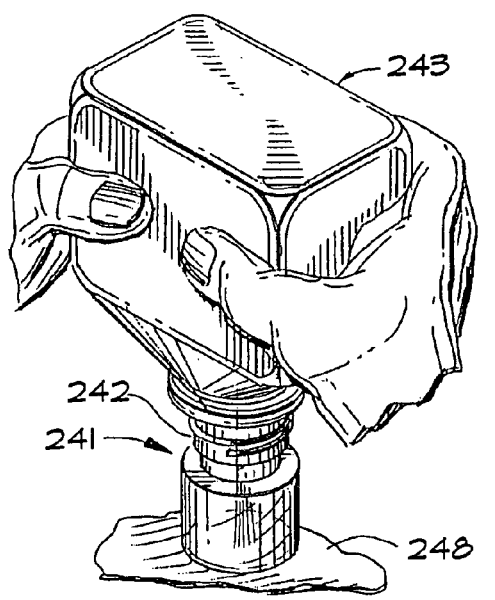
FIG. 5A is a perspective view of another preferred embodiment of a splash shield according to the present invention, which splash shield is shown fitted into the neck of a bottle of the type containing irrigation fluid.
Figure 5B:
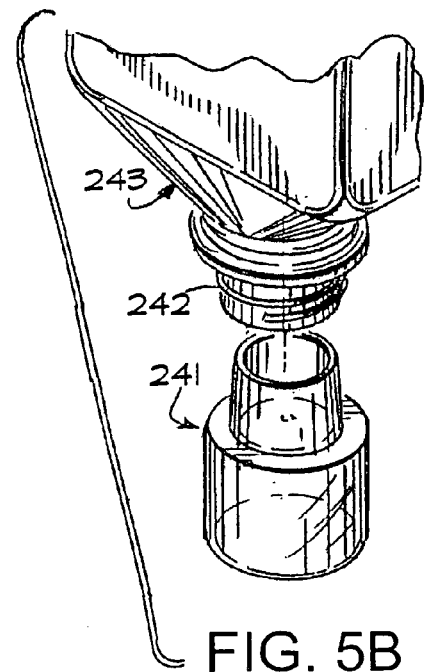
FIG. 5B is a perspective view of the embodiment of FIG. 5A shown detached from the illustrated bottle.
Figure 5C:
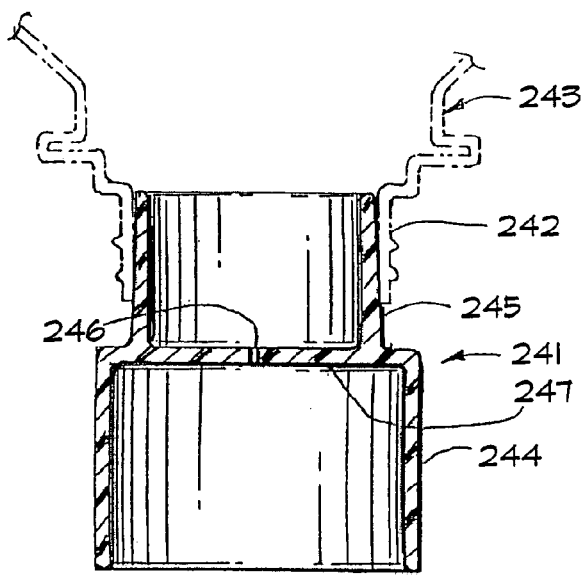
FIG. 5C is a sectional view through the center of the embodiment of FIG. 5A showing structural details and showing its fit in the illustrated bottle (which is in dotted lines).
Figure 5D:
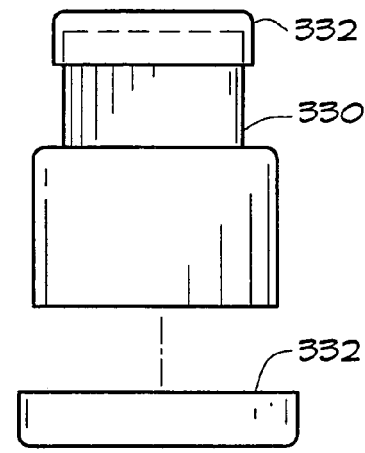
FIG. 5D is a side view of the embodiment of FIG. 5A shown with an end cap attached on the top end and an end cap detached from the bottom end of the splash shield.

FIG. 5A is a perspective view of another preferred embodiment of a splash shield 241 according to the present invention, which splash shield 241 is shown fitted into the neck 242 of a bottle 243 of the type containing irrigation fluid. FIG. 5B is a perspective view of the splash shield 241 of FIG. 5A shown detached from the illustrated bottle 243. FIG. 5C is a sectional view through the center of the splash shield 241 of FIG. 5A showing structural details and showing its fit in the illustrated bottle 243 (which is in dotted lines). Splash shield 241 (as shown best in FIG. 5C) is stepped from a larger-diameter cylindrical portion 244 to a smaller-diameter portion 245 that is sized with external taper to friction fit as shown within neck 242 of bottle 243 (in dotted lines in FIG. 5C). Thus, for example, squeezing of a squeeze bottle 243 brings irrigation fluid into upper portion 245, from where it may be forced through a hole 246 in dividing surface 247 to impinge upon skin portion 248 (see FIG. 5A) with lower portion 244 acting to shield say, a user, from fluid or debris from a wound on skin portion 248. FIG. 5D is a side view of a splash shield with an end cap 332 attached on the top end and an end cap 332 detached from the bottom end of splash shield 330. Preferably, end cap 332 assists in protecting internal sterility of the splash shield. End cap 332 also creates a closed pocket within splash shield, which can be used for example to store other items such as wound treatment products and devices.

Figure 6A:
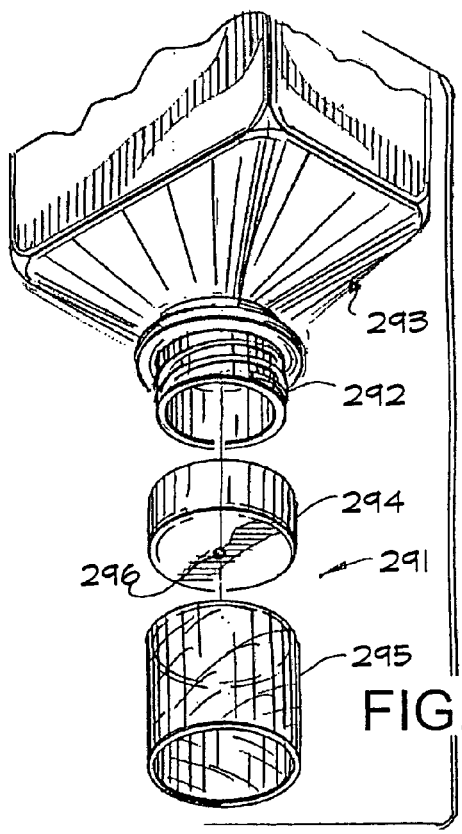
FIG. 6A is an exploded perspective view of yet another preferred embodiment of the splash shield of the present invention, showing the end of an irrigation bottle, a bottle adapter to control the irrigation stream, and a tubular splash shield element.
Figure 6B:
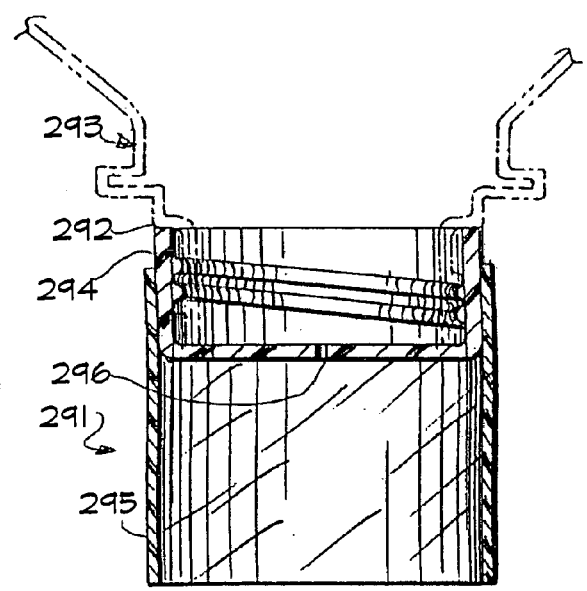
FIG. 6B is a sectional view of the embodiment of FIG. 6A illustrating the details with the splash shield connected to the bottle (shown in dotted lines).

FIG. 6A is an exploded perspective view of yet another preferred embodiment of the splash shield 291 of the present invention, showing the end 292 of an irrigation bottle 293, a bottle adapter 294 to control the irrigation stream, and a tubular splash shield element 295. FIG. 6B is a sectional view of the splash shield 291 of FIG. 6A illustrating the details with the splash shield 291 connected to the bottle 293 (shown in dotted lines). As shown, to use the splash shield 291, it is preferred to friction fit adapter 294 over the end 292 of bottle 293, and to friction fit splash shield element 295 over the bottom of adapter 294. Then fluid from bottle 293 may be forced into adapter 294, through hole 296, and into the tubular splash shield element areas for wound irrigation.

FIG. 7A is a perspective view of a preferred embodiment of a combined splash shield and irrigation squeeze tube 301 according to the present invention. FIG. 7B is a partial perspective view of the irrigation squeeze tube 301 of FIG. 7A, partially cut away to show its use with cap 302 removed. Toothpaste-type squeeze tube portion 299 has a built-in or a removable transparent wound irrigation shield portion 303. An outlet 304 to allow fluid egress or to allow attachment to a vacuum source (not shown) may be optionally provided for the advantages enumerated previously. Cap 302 is made long enough for removal or attachment to tube portion 299 with shield portion 303 in place. In operation, the tube portion 299 is squeezed, thus forcing irrigation fluid onto a wound, as previously set forth generally. Having a removable shield portion 303 is preferred if cap 302 is to be provided with nozzle 305 adaptations or adaptors (as taught previously herein) that allow modulation and that must be accessed easily in a sterile fashion, particularly if a simple, cheap, and easily available component such as a transparent plastic PVC tubing were used.

FIG. 8A a is front view illustrating yet another preferred embodiment of a splash shield 271 according to the present invention, showing a spike connector 272 attached to a squeeze bag 273 and also fitted into a cylindrical splash shield element 274. FIG. 8B is a perspective view of the splash shield 271 of FIG. 8A, showing the spike connector 272 separated from the cylindrical splash shield element 274. FIG. 8C is a partial sectional view showing the connection details with the spike connector 272 attached to the cylindrical splash shield element 274. Spike connector 272 is a component of the type commonly used in creating an IV spike dripping chamber for modulating the administration of IV fluid through IV tubing, as shown (embodying herein wherein such spike comprises an IV-spike connecter, unitary with such body). Splash shield element 274 may be made from standard PVC tubing to create an easily produced IV spike connector wound irrigation splash shield 271. By using simple available components in a new configuration and method, the tool investment would be minimized. It would also provide users with familiar equipment and parts that would reduce apprehension over using a new device. Providing this splash shield 271 permanently connected would provide significant advantages in some situations as described above. There may be an optional outlet contour or aperture 275 (see FIG. 8B) which can function as an exit opening for effluent irrigation fluid or for the attachment of a vacuum connector. In addition, the tubing comprising splash shield element 274 may be flexible to prevent discomfort and trauma and to facilitate a better seal against the skin. When splash shield 271 is connected to bag 273, squeezed irrigation fluid 276 is forced through spike conduit 277 and through hole 278 in dividing surface 279, from where it enters attached splash shield element 274 for the described usages in wound irrigation.

Figure 9A:
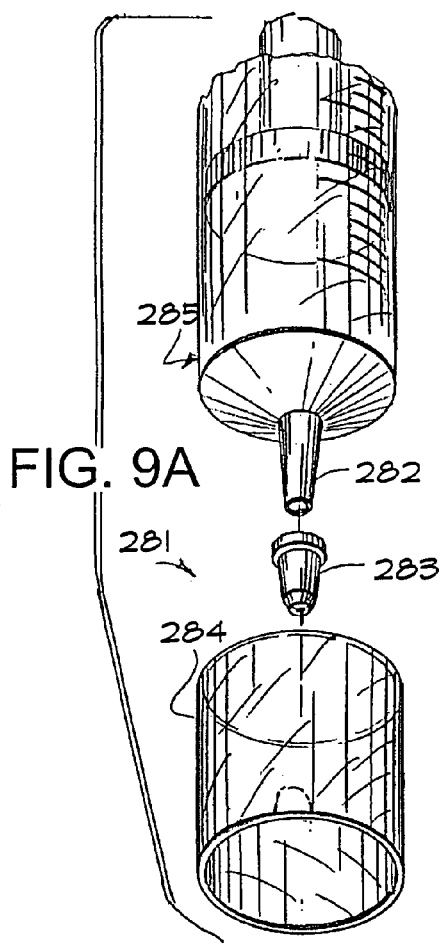
FIG. 9A is an exploded perspective view of yet another preferred embodiment of the splash shield of the present invention, showing a syringe-type end, a syringe adapter to control the irrigation stream, and a tubular splash shield element.
Figure 9B:
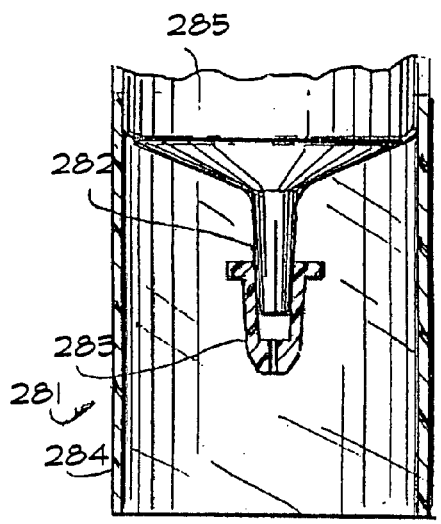
FIG. 9B is a sectional view of the embodiment of FIG. 9A illustrating the details with the parts connected.

FIG. 9A is an exploded perspective view of yet another preferred embodiment of the splash shield 281 of the present invention, showing a syringe-type tip 282, a syringe adapter 283 to control the irrigation stream, and a tubular splash shield component 284. FIG. 9B is a sectional view of the splash shield 281 of FIG. 9A illustrating the details with the parts connected. This arrangement provides a separate transparent shield component 284 which may be connected over a syringe body 285 to easily and quickly transform a standard syringe into a shield wound irrigation delivery device as shown in FIG. 9B. One might want optionally to add adaptor 283 to the syringe tip 282 to modulate the flow. Providing a removable wound irrigation splash shield component 284 over the syringe body 285 would facilitate this by eliminating the need to reach into a potentially narrow, tight fitting sterile space to manipulate, position and exchange connectors.

Figure 10B:
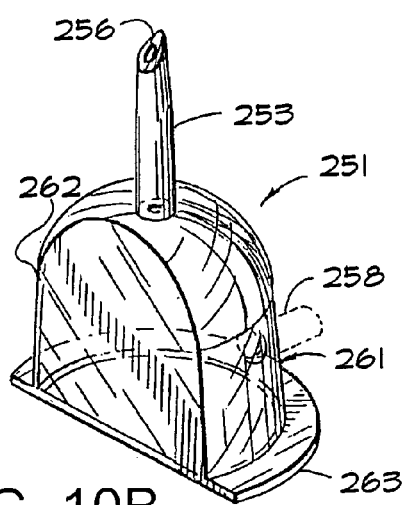
FIG. 10B is an enlarged (over FIG. 10A) perspective view of the embodiment of FIG. 10A.
Figure 10A:
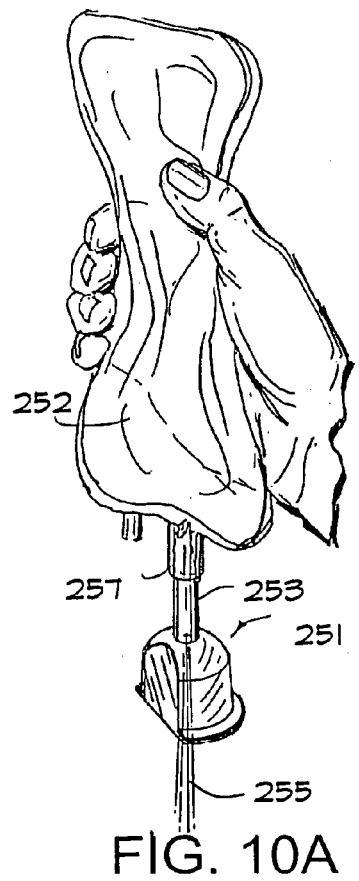
FIG. 10A is a perspective view of yet another preferred embodiment of a splash shield according to the present invention shown attached to an IV-type squeeze bag by way of the IV spike connector of this embodiment.

FIG. 10A is a perspective view of yet another preferred embodiment of a splash shield 251 according to the present invention shown attached to an IV-type squeeze bag 252 by way of the IV spike connector 253 of splash shield 251. FIG. 10B is an enlarged (over FIG. 10A) perspective view of the splash shield 251 of FIG. 10A. FIG. 10C is sectional side view of the splash shield 251 of FIG. 10A illustrating the structural details thereof. FIG. 10D is a bottom view of the splash shield 251 of FIG. 10A. Wound irrigation splash shield 251 is preferably transparent and engineered to be sterilizable and disposable as is commonly done in the medical industry. IV spike connector 253 (resembling a commonly available "IV spike") is a male connector with an inner conduit 254 for fluid 255 and a tapered pointed end 256 fits into the outlet end connector 257 of a fluid container such as a sterile IV solution bag 252 as shown in FIG. 10A. Optionally, if desired, there might be an outlet 258 (dotted lines in FIG. 10B) for the attachment to a vacuum source. In operation, fluid 255 is squeezed though conduit 254 of IV spike connector 253, from where it is forced through hole 259 of dividing surface 260 to form an irrigation stream through shield portion 261 (preferably shaped as shown, where, to better cover body wounds on appendages, as before mentioned, the preferred ratio of a maximum length of the open bottom end compared to a maximum width of such bottom end is at least 1.5:1.0) of wound irrigation splash shield 251. As shown, it is preferred that one (bottom) edge of the shield portion 261 be substantially linear so to provide a stable pivoting surface to promote a linearly directed irrigation stream. Also, one side 262 of shield portion 261 may preferably be substantially planar so as to increase the user's visibility of the irrigation process. Also, the irrigation stream may preferably be "off-center" to promote proximity to wall surfaces; that would allow better visualization. Also, it is preferred to provide a ledge 263 as shown at the bottom of shield portion 261 for better sealing against a skin portion when desired and for increasing the protective area of the device without increasing the width of the splash area required to form a seal.

FIG. 11A is a side elevation view of a preferred embodiment of the medical splash shield device 52 of the present invention. Preferably the device may be made of an inexpensive disposable transparent biocompatible medical grade plastic such as a US FDA class VI PVC or polycarbonate that may also be sterile to prevent wound infection. FIG. 11B is a top plan view of the splash shield device 52 of FIG. 11A. FIG. 11C is a perspective view of the splash shield device 52 of FIG. 11A showing it in a restrained position, as on a portion of nearby equipment 19. FIG. 11D is a side sectional view of the splash shield device 52 of FIG. 11A, illustrating its operation. As shown, the medical splash shield device 52 of this preferred embodiment includes proximal outlet 14 (embodying herein an output opening structured and arranged to allow suctioning excess irrigation fluid from within such body; wherein such output opening is structured and arranged to draw excess irrigation fluid from such splash portion toward a location approximately at a position symmetrically opposed (with respect to such maximum height dimension) from the location of such input opening), and a distal opening 17 for entry of the wound-washing fluid, shown as irrigation fluid 57. Preferably, distal opening 17 is located substantially lower than the maximum height dimension, as shown. The smooth rounded body 50 has an opening, as shown, which is either rectangular with rounded ends or a similar long oval in shape (seen most clearly in FIG. 11B). Most of the illustrated bottom opening is portion 67 in a flat plane; but the distal end portion 51 of the bottom opening is in a plane coming upwards from the plane of portion 67 at about an angle of 30 degrees, as shown. A clip restraint 23 is preferably located near the top of the body 50 and protruding from the body 50 at about a parallel relationship to the protrusion of outlet 14. As shown, the proximal end wall 70 of body 50 is relatively vertical while the distal end wall 71 of body 50 rises very gradually at no more than about 45 degrees from the horizontal. The outlet 14 is located near the bottom-opening portion 67 and near the bottom of substantially vertical proximal end wall 70. The distal opening 17 preferably functions as an inlet and is located approximately centrally on the distal end wall 71.

With reference to FIG. 11D, the described preferred geometry permits the following operation (as shown) of splash shield device 52. The problems of prior art splash shield devices like that of FIG. 17 are overcome with the embodiment of FIGS. 11A-E. The flushing irrigation fluid 57, as from syringe 55, irrigates wound 54 with a flow that flushes the debris toward and into vacuum line 10 by way of inlet end 12. Note that the placement of inlet end 12 near the flesh 53 portion of the splash shield device 52 assists in an efficient unidirectional flush flow to efficiently clean the wound 54 and remove debris and excess fluid (as shown). Preferably distal opening 17 is angled to assist in directing irrigation fluid at an oblique angle from vertical, so that a greater horizontal component of force from the fluid is imparted to flush debris out of the wound (embodying herein wherein such input opening is structured and arranged to assist in directing irrigation fluid at an oblique angle from vertical). Also, the elongated bottom shape (in an appropriate size) is more suited than a circular bottom shape for shielding and collecting flushing fluids on non-flat body parts such as arms, fingers, and feet. It is also noted that the relief afforded by the raised portion 51 of the shield bottom assists in providing more air flow (from an efficient direction) as needed for good flushing. And, as illustrated by FIG. 11E (a side sectional view of the embodiment of FIG. 11A), the user may still press the splash shield device 52 toward the flesh 53 to operate the shield with relief closure as desired. This non-flat contour also assists in the pivoting of the device and the irrigation jet along the wound 54, changing the angle of the jet in relation to a position or location on the skin in a linear fashion.

FIG. 11F is a perspective view of a preferred alternate usage of the splash shield device 52 of the type of FIG. 11A, further illustrating siphoning of irrigation fluid 57 from a fluid bottle 59 by way of tubing 60. Vent opening 61 is preferably provided in container cap 80 for well-known reasons.

FIG. 12A is a side sectional view of an alternate preferred embodiment of the splash shield device 52 of the present invention, illustrating its operation incorporating an inlet swivel structure permitting better direction of impingement of the saline or other irrigation fluid 57, even for impinging along a wound length direction (as for wound 54) (embodying herein wherein such input opening comprises: a swivel structured and arranged to allow a user to direct a stream of irrigation fluid to selected portions of the skin of a patient; wherein such swivel comprises an attacher structured and arranged to allow attachment of a source of irrigation fluid to such swivel). The details of the inlet swivel structure are best shown in FIGS. 12B-C. FIG. 12B is a partial expanded sectional view of the embodiment of FIG. 12A, illustrating swivel detail. FIG. 12C is an exploded perspective view further illustrating the swivel detail of the embodiment of FIG. 12A. As shown, inlet swivel 62 containing distal opening 17 rides and may rotate in swivel socket 63, which socket is fixed in place by fixed attachment with the distal end wall 71 of splash shield device 52. When the tip 158 of syringe 55 is inserted into distal opening 17, the orifice nozzle 58 of inlet swivel 62 is enabled (see FIG. 12B) to direct fluid 56 into the splash shield as shown. The arrangements of FIGS. 11A, 11B, 11C, 11D, 11E, 11F, 12A, 12B and 12C embody herein a body structured and arranged to contain irrigation fluid, wherein such body has a maximum height dimension, and an input opening structured and arranged to allow the irrigation fluid into such body, wherein such input opening is located at a substantially lower position than such maximum height dimension; and further embody herein wherein a bottom peripheral circumference of such body has an oval-like shape; and further embody herein wherein such body includes at least one bottom opening; wherein the ratio of a maximum length of such at least one bottom opening compared to a maximum width of such at least one bottom opening is at least 1.5:1.0.

FIG. 13A is a perspective view of yet another preferred embodiment of a splash shield 311 according to the present invention. Splash shield 311 is shown with an inlet port 312 attached to an irrigation syringe 313 and a vacuum connector port 314 attached to a vacuum line 315. FIG. 13B is a side view of the splash shield 311 of FIG. 13A, shown attached to the irrigation syringe 313. FIG. 13C is a front view of the splash shield 311 of FIG. 13A, with the irrigation syringe 313 in dotted lines. FIG. 13D is a side sectional view of the splash shield 311 of FIG. 13A showing the structural details and fluid flow directions. FIG. 13E is a top view of the splash shield 311 of FIG. 13A. FIG. 13F is a partial sectional view through the section 13F-47F of FIG. 13B. FIG. 13G is a bottom view of the splash shield 311 of FIG. 13A.

The illustrated preferred embodiment of splash shield 311 has multiple inlet ports 312 and 312a, with varying internal configurations so that various different kinds of syringes or other fluid containers may be attached and variations in spray fineness may be had. Inlet ports 312 and 312a have male and female connection potential to allow for multiple user preferences with a single manually-operated splash shield 311. Alternately to the inlet port configurations illustrated, such ports may in certain applications protrude into the splash shield 311 or be located within the wall of the splash shield 311. Vacuum connector port 314 is located adjacent base 318 of the splash shield 311 to assist in removal of fluid at the skin surface. As shown, a groove 319 at each bottom side of splash shield 311 acts as a conduit for allowing air and irrigation fluid and debris to be transported to vacuum connector port 314 when downward pressure against the skin is applied while there is a vacuum pull. The grooves 319 form an incomplete seal on a contact surface and widen the base of the splash shield 311, with the groove 319 against the skin becoming an aperture through which such contaminated fluid can be removed. Such groove(s) 319 are preferred to be located near the base of the splash shield 311 to prevent or minimize any visual obstruction caused by the vacuum apparatus features for an observer looking from above (embodying herein an output nozzle structured and arranged to attach to a vacuum line; a conduit structured and arranged to direct suction flow across such splash portion toward such output nozzle; wherein such conduit comprises at least one channel along a periphery of such body extending from such output nozzle to a location approximately at a position symmetrically opposed from the location of such input opening).

The inlet ports 312 and 312a are preferably made to extend in parallel fashion with the vacuum connector port 314 to simplify manufacturing tooling complexity and cost. It is noted that grooves 319 are preferably located adjacent the outer perimeter 321 of the splash shield 311, thus increasing the total surface area of the splash shield 311 without compromising the smaller area that can form an inner protective or operational seal against the skin for wound irrigation protection, particularly for areas of small surface area or sharp contour. For example, over the sharp edge of the chin, one could form an adequate seal with the inner perimeter formed by the inner wall of the groove(s) 319. The lateral outer edges of the grooves would increase the effective surface area protection beyond that formed within the inner seal. This device preferably has a longitudinally tapered base 318 or perimeter 321 to facilitate attachment over the skin; and it preferably has a relief port or contour 325 to facilitate the directional outflow of irrigation effluent or to allow the inflow of gas to facilitate the vacuum of irrigation fluid. It is noted that, if desired for certain uses, the vacuum connector port 314 may be eliminated; and the illustrated device can be operated with or without a vacuum source connected. It is noted that the inlet on the illustrated device is off center, thus providing a design that permits maximum pivoting ability while maintaining efficient shielding. It is also preferred to have flat side edges 318a and 318b of base 318 to maximize stability of the device when pivoted along the edge, as when one is irrigating along a linear laceration.

Figure 14A:
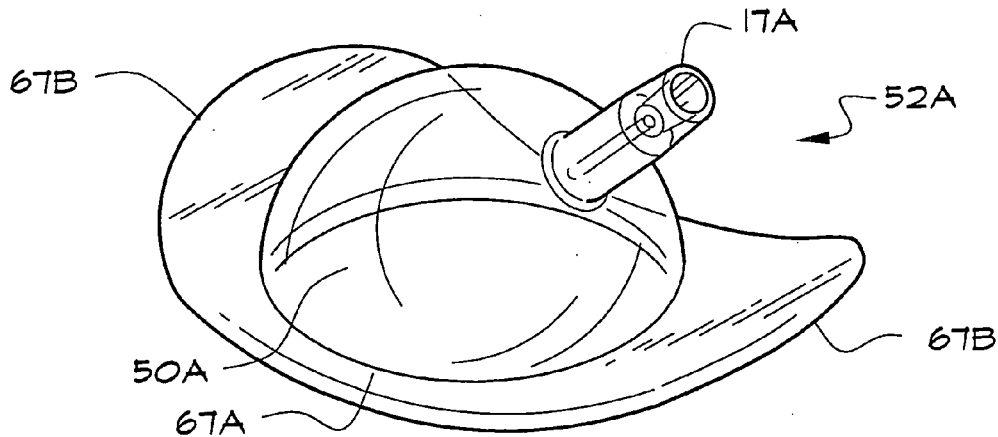
FIG. 14a is a perspective view of yet another preferred embodiment of a splash shield according to the present invention.
Figure 14B:
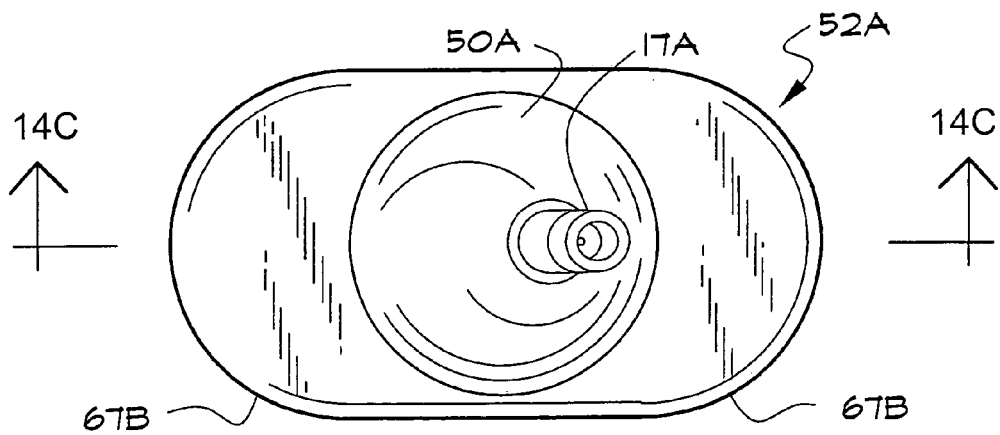
Figure 14C:
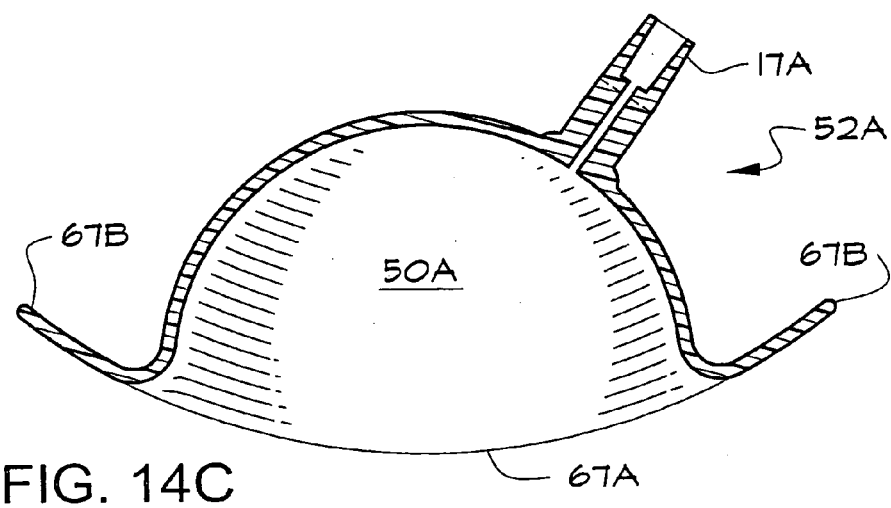

FIGS. 14A (a perspective view), 14B (a top view), and 14C (a sectional view through the section 14C of FIG. 14B) illustrate another preferred embodiment of a splash shield 52A having many common advantages, arrangements and functions with splash shield device 52, with a few exceptions noted as follows. Bottom portion 67A preferably has a rounded periphery, preferably generally oval or circular, as shown. As shown, extending from this periphery is an extension 67B, as shown, with which to assist rocking of splash shield 52A to better direct the splash stream along the wound and also which performs a function of protecting the fingers and hands of the user from irrigation fluid and wound debris. As shown, bottom portion 67A also implements the "rocker" profile, having a non-planar bottom opening, and non-planar extension 67B. Preferably bottom portion 67A and extension 67B are "saddle-shaped", as shown (embodying herein a transparent body structured and arranged to assist in protecting a user from contact with irrigation fluid directed at a patient's wound; an irrigation-source connecter structured and arranged to connect such body, at a first end of such body, to a source of irrigation fluid; wherein such transparent body comprises at least one bottom opening wherein a bottom periphery of such at least one bottom opening is substantially non-planar; and further embodying herein wherein such bottom peripheral circumference is structured and arranged to allow rocking such body; and further embodying herein wherein such bottom peripheral circumference is saddle-shaped).

What is claimed is:

1. A splash shield system, related to protecting a user from contact with irrigation fluid directed at a patient's wound, comprising:
   a) at least one body; comprising at least one first end and at least one second end;

b) wherein said at least one body comprises at least one first inner hollow;
c) wherein said at least one second end is open to said at least one first inner hollow;
d) at least one irrigation-source connector structured and arranged to connect said at least one irrigation-source connector, at said at least one first end, to at least one wide mouth wound irrigation squeeze bottle; and
e) at least one adapter structured and arranged to facilitate at least one connection between said at least one body and at least one syringe.

2. The splash shield system according to claim 1 wherein said at least one first inner hollow comprises at least one substantially transparent wall portion structured and arranged to help protect the user from contact with the irrigation fluid.

3. The splash shield system according to claim 1 wherein said at least one irrigation-source connector comprises at least one inner diameter between about ⅘ inches and about 1¾ inches.

4. The splash shield system according to claim 1 wherein said at least one irrigation-source connector comprises at least one inner diameter between about 1.4 inches and about 1.6 inches.

5. The splash shield system according to claim 1 wherein said at least one body is substantially transparent.

6. The splash shield system according to claim 1 wherein said at least one body, said at least one irrigation-source connector, and said at least one first inner hollow all consist essentially of one monolithic piece.

7. The splash shield system according to claim 1 wherein said at least one irrigation-source connector comprises helical threads.

8. The splash shield system according to claim 1 further comprising at least two holes adapted to dispense the irrigation fluid towards the wound.

9. The splash shield system according to claim 1 wherein said at least one body is sterile.

10. The splash shield system according to claim 1 further comprising
a) at least one second inner hollow;
b) wherein said at least one second inner hollow comprises said at least one irrigation-source connector;
c) wherein said at least one first inner hollow comprises at least one substantially transparent wall portion structured and arranged to help protect the user from contact with the irrigation fluid.

11. The splash shield system according to claim 10 wherein said at least one irrigation-source connector comprises at least one inner diameter between about 1.4 inches and about 1.6 inches
and wherein said at least one body, said at least one irrigation-source connector, and said at least one inner hollow all consist essentially of one monolithic piece;
and wherein said at least one irrigation-source connector comprises helical threads.

12. The splash shield system according to claim 10 further comprising at least two holes adapted to dispense the irrigation fluid towards the wound.

13. The splash shield system according to claim 10 wherein said at least one body is sterile.

14. The splash shield system according to claim 10 comprising an elongated nozzle.

\* \* \* \* \*